US00PP24380P2

(12) United States Plant Patent
Giesen

(10) Patent No.: US PP24,380 P2
(45) Date of Patent: Apr. 8, 2014

(54) ***ARGYRANTHEMUM* PLANT NAMED 'CHQZ0001'**

(50) Latin Name: *Argyranthemum frutescens*
Varietal Denomination: CHQZ0001

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 62 days.

(21) Appl. No.: 13/573,403

(22) Filed: Sep. 13, 2012

(51) Int. Cl.
*A01H 5/00* (2006.01)

(52) U.S. Cl.
CPC ..... *A01H 5/00* (2013.01)
USPC ..... Plt./406

(58) Field of Classification Search
CPC ..... A01H 5/00; A01H 4/00; A01H 1/00; A01H 1/04; A01H 1/06
USPC ..... Plt./406
See application file for complete search history.

*Primary Examiner* — Annette Para
(74) *Attorney, Agent, or Firm* — Joshua L. Price

(57) ABSTRACT

A new *Argyranthemum* plant named 'CHQZ0001' particularly distinguished by the semi-double intense red-purple ray floret color, good color retention under high light conditions, with an upright and compact plant habit and medium green foliage color.

1 Drawing Sheet

Latin name of the genus and species of the plant claimed: *Argyranthemum frutescens.*

Varietal denomination: 'CHQZ0001'.

BACKGROUND OF THE NEW PLANT

The present invention comprises a new *Argyranthemum*, botanically known as *Argyranthemum frutescens*, and hereinafter referred to by the variety name 'CHQZ0001'.

'CHQZ0001' is a product of a planned breeding program. The new cultivar has semi-double intense red-purple ray floret color, has good color retention under high light conditions, with an upright and compact plant habit and medium green foliage color.

'CHQZ0001' originated from an open-pollinated hybridization made in the summer of 2007 in a greenhouse in Enkhuizen, The Netherlands. The female parent was the unpatented commercial variety named 'Meteor Pink', with smaller more rose colored flowers and lighter green foliage than that of 'CHQZ0001'.

The male parent of 'CHQZ0001' was unknown. The resultant seed was sown in a greenhouse in Enkhuizen, The Netherlands in September 2007.

'CHQZ0001' was selected as one flowering plant within the progeny of the stated cross in January 2008 in Enkhuizen, The Netherlands.

The first act of asexual reproduction of 'CHQZ0001' was accomplished when vegetative cuttings were propagated from the initial selection in January 2008 in a greenhouse in Enkhuizen, The Netherlands.

BRIEF SUMMARY OF INVENTION

Horticultural examination of plants grown from cuttings of the plant initiated in January 2008, and continuing thereafter, has demonstrated that the combination of characteristics as herein disclosed for 'CHQZ0001' are firmly fixed and are retained through successive generations of asexual reproduction.

'CHQZ0001' has not been observed under all possible environmental conditions. The phenotype may vary significantly with variations in environment such as temperature, light intensity, and day length.

Plant Breeder's Rights for this cultivar were applied for in Canada on Nov. 1, 2011 (11-7410) and at Community Plant Variety Office on Jul. 20, 2012 (2012/1617). 'CHQZ0001' has not been made publicly available more than one year prior to the filing of this application.

The following traits have been repeatedly observed and are determined to be basic characteristics of the new variety. The combination of these characteristics distinguishes this Argyranthemum as a new and distinct variety.

BRIEF DESCRIPTION OF THE PHOTOGRAPHS

Figure 1:
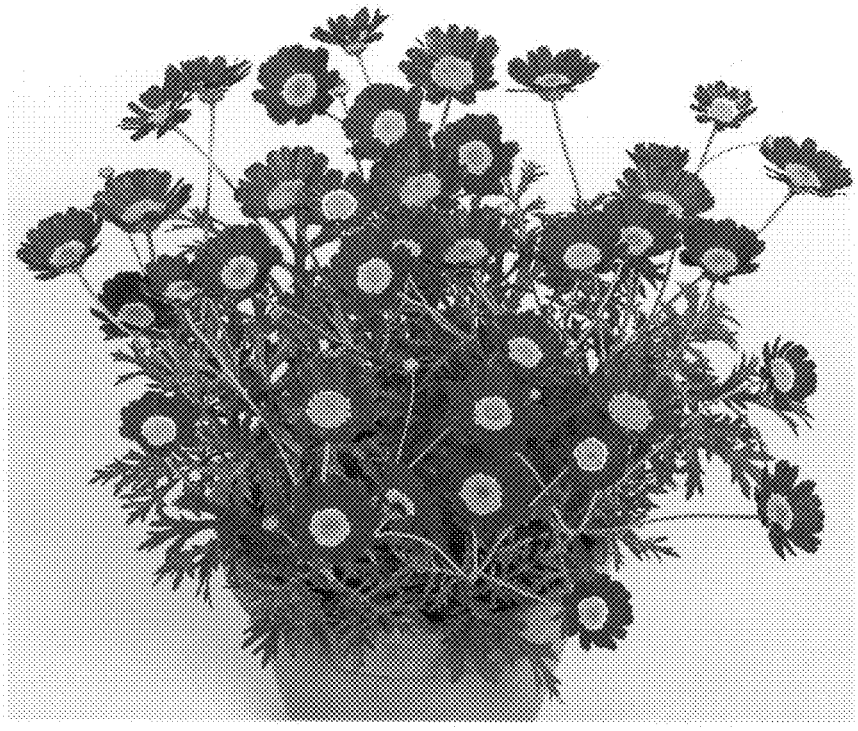
Figure 2:
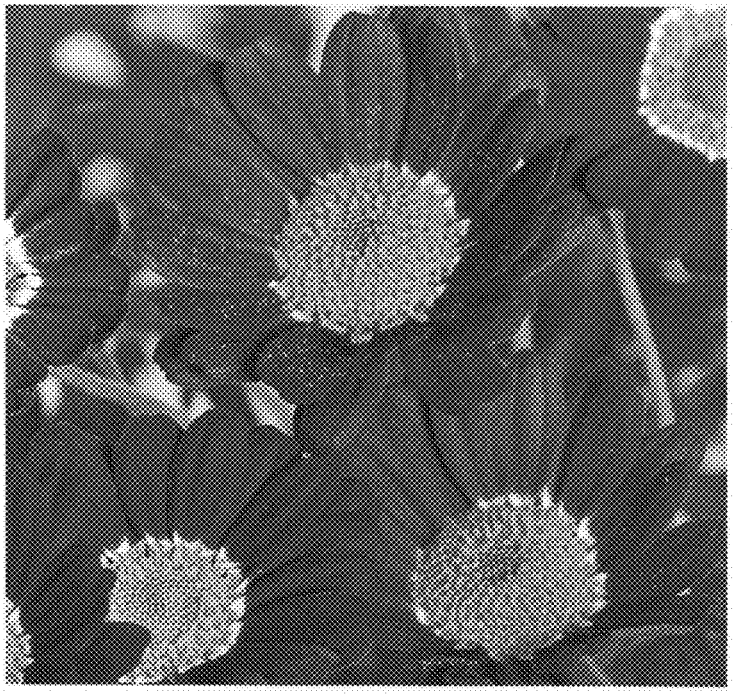

The accompanying photographic drawing shows typical flower and foliage characteristics of 'CHQZ0001' with colors being as true as possible with an illustration of this type. The photographic drawing shows in FIG. 1 a flowering plant of the new variety and in FIG. 2 a close-up of the inflorescences.

DETAILED BOTANICAL DESCRIPTION

The plant descriptions and measurements were taken in Enkhuizen, The Netherlands in early August 2012 under outdoor natural light. The plants used were about 22 weeks of age, growing in 20 cm×15 cm×1 meter long window boxes, outside in full sun.

The aforementioned photographs were taken in Enkhuizen, The Netherlands in April 2009 in a greenhouse. These plants were approximately 12 weeks of age.

Color references are made to The Royal Horticultural Society Colour Chart (R.H.S.) 2001.

TABLE 1

DIFFERENCES BETWEEN THE NEW VARIETY 'CHQZ0001' AND A MOST SIMILAR VARIETY

| | 'CHQZ0001' | 'SUPA742' (U.S. Plant Pat. No. 18,435) |
|---|---|---|
| Ray floret color: | More red tones | Less red/more rose tones |
| Disc diameter: | Smaller | Larger |
| Peduncle length: | Shorter | Longer |

Plant:

*Form, growth and habit.*—Mounded and compact, freely branching with mostly upright peduncles.

*Plant height.*—24.0 cm.

*Plant height (inflorescence included).*—35.0 cm.

*Plant width.*—30.0 cm.

Roots:

*Number of days to initiate and produce roots.*—4-6 days at about 22 degrees C.

*Type.*—Fine, fibrous, free branching.

*Color.*—RHS N155B.

Foliage:

*Arrangement.*—Alternate.

*Immature, leaf color, upper surface.*—Between RHS 143B and RHS 143C.

*Immature, leaf color, lower surface.*—RHS 143C.

*Mature, leaf color, upper surface.*—RHS 137B.

*Mature, leaf color, lower surface.*—RHS 137C.

*Length.*—5.5 cm.

*Width.*—4.0 cm.

*Shape.*—Ovate.

*Base shape.*—Attenuate.

*Shape.*—Apiculate.

*Margin.*—Pinnatisect.

*Texture, upper surface.*—Glabrous.

*Textures, lower surface.*—Glabrous.

*Color of veins, upper surface.*—RHS 143B.

*Color of veins, lower surface.*—RHS 143B.

*Pattern of veining.*—Pinnate.

*Petiole color.*—RHS 143B.

*Length.*—0.2 cm.

*Diameter.*—0.3 cm.

*Texture.*—Glabrous.

Stem:

*Quantity of main branches per plant.*—22.

*Color of stem.*—RHS 144C.

*Length of stem.*—13-17.0 cm.

*Diameter.*—0.5 cm.

*Length of internodes.*—1-3.0 cm.

*Texture.*—Glabrous.

*Color of peduncle.*—RHS 144D.

*Length of peduncle.*—1-3.0 cm.

*Peduncle diameter.*—0.25 cm.

*Texture.*—Glabrous.

Inflorescence:

*Type.*—Daisy-type inflorescences; disc and ray florets develop acropetally on a capitulum. Inflorescences held upright and outwardly on terminal peduncles.

*Quantity of inflorescences per plant.*—About 75.

*Lastingness of individual blooms on the plant.*—About 10 days.

*Fragrance.*—Slightly spicy.

Bud (just when opening/showing color):

*Color.*—RHS 59B.

*Length.*—1.1 cm

*Width.*—1.1 cm.

*Shape.*—Rounded.

Immature inflorescence:

*Diameter.*—2.5 cm.

*Color of ray florets, upper surface.*—RHS 60B with RHS 144C basally.

*Color of ray florets, lower surface.*—RHS 60C.

*Color of disc floret, outer surface.*—RHS 149D, with RHS 3C apex and RHS 178A margins, and RHS 155B basally.

Mature inflorescence:

*Diameter.*—3.2 cm.

*Depth.*—1-1.3 cm.

*Total diameter of disc.*—1.1 cm.

*Receptacle color.*—RHS 141C to RHS 144D.

*Receptacle height.*—1.1 cm.

*Receptacle diameter.*—1.0 cm.

Ray florets:

*Average quantity of florets.*—19-21 in 2 whorls.

*Color of florets, upper surface.*—RHS 59C with RHS 144C basally.

*Color of florets, lower surface.*—RHS 60C.

*Length.*—1.3 cm.

*Width.*—0.5 cm.

*Shape.*—Oblanceolate.

*Apex shape.*—Rounded.

*Base shape.*—Attenuate.

*Margin.*—Entire.

*Texture, upper surface.*—Glabrous.

*Textures, lower surface.*—Glabrous.

Disc florets:

*Average quantity of florets.*—About 42.

*Color of florets.*—RHS 149D, with RHS 3C apex and a little RHS 178A on the margins, and RHS 155B basally.

*Length.*—0.6 cm.

*Width.*—0.1 cm.

*Shape.*—Tubular, elongated.

*Apex shape.*—Acute, 5 pointed.

*Texture, inner surface.*—Glabrous.

*Textures, outer surface.*—Glabrous.

Phyllaries:

*Quantity.*—About 18.

*Color, upper surface.*—RHS 141C.

*Color, lower surface.*—RHS 143C.

*Length.*—0.25 cm.

*Width.*—0.35 cm.

*Shape.*—Laneolate.

*Apex shape.*—Acuminate.

*Base.*—Truncate.

*Margins.*—Entire.

*Texture, upper surface.*—Glabrous.

*Texture, lower surface.*—Glabrous.

Reproductive organs:

*Pistil.*—1, found on both types of florets.

*Length.*—0.6 cm.

*Style color.*—RHS 154D.

*Style length.*—0.2 cm.

*Stigma color.*—RHS 12A.

*Stigma shape.*—Bi-parted.

*Ovary color.*—RHS 155A.

*Ovary length.*—0.15 cm.

*Ovary width.*—0.1 cm.

*Stamens.*—4, found on only on the disc florets.

*Color of filaments.*—RHS 1D.

*Length filaments*.—0.15 cm.
*Anther color*.—RHS 185A.
*Anther length*.—0.1 cm.
*Anther shape*.—Oval.
*Color of pollen*.—RHS 7B.
*Pollen amount*.—Normal.
*Fertility/seed set*.—Has not been determined to date.
*Disease/pest resistance*.—Has not been determined to date.

What is claimed is:

1. A new and distinct variety of *Argyranthemum* plant named 'CHQZ0001' substantially as illustrated and described herein.

* * * * *